United States Patent
Taskinen et al.

(10) Patent No.: US 9,138,370 B2
(45) Date of Patent: Sep. 22, 2015

(54) MASSAGE APPARATUS

(75) Inventors: Leo Tapani Taskinen, Helsinki (FI); Timo Juhani Niskanen, Lahela (FI)

(73) Assignee: HLD Healthy Life Devices Ltd., Espoo (FI)

( * ) Notice: Subject to any disclaimer, the term of this patent is extended or adjusted under 35 U.S.C. 154(b) by 1413 days.

(21) Appl. No.: 11/994,511

(22) PCT Filed: Oct. 24, 2006

(86) PCT No.: PCT/FI2006/000343
§ 371 (c)(1),
(2), (4) Date: Jan. 3, 2008

(87) PCT Pub. No.: WO2007/051896
PCT Pub. Date: May 10, 2007

(65) Prior Publication Data
US 2008/0200778 A1  Aug. 21, 2008

(30) Foreign Application Priority Data

| Oct. 31, 2005 | (FI) | 20051102 |
| Mar. 7, 2006 | (FI) | 20060222 |
| Aug. 1, 2006 | (FI) | 20060708 |

(51) Int. Cl.
*A61B 5/00* (2006.01)
*A61H 7/00* (2006.01)

(52) U.S. Cl.
CPC ............. *A61H 7/005* (2013.01); *A61B 5/441* (2013.01); *A61H 7/008* (2013.01); *A61H 2201/10* (2013.01); *A61H 2207/00* (2013.01); *A61H 2230/00* (2013.01); *A61H 2230/65* (2013.01)

(58) Field of Classification Search
CPC ........... A61H 15/0085; A61H 15/0176; A61H 15/018; A61H 15/5058; A61B 5/445; A61B 5/441; A61B 5/442

USPC .......... 600/300, 309, 306; 601/6–14, 118–134
See application file for complete search history.

(56) References Cited

U.S. PATENT DOCUMENTS

| 4,729,368 A * | 3/1988 | Guitay ......................... 601/123 |
| 5,885,232 A | 3/1999 | Guitay |

(Continued)

FOREIGN PATENT DOCUMENTS

| CH | 686221 | 2/1996 |
| EP | 1045685 | 6/2002 |

(Continued)

OTHER PUBLICATIONS

Latrenta, Gregory S., "Endermologie versus Liposuction with External Ultrasound Assist." Aesthetic Surgery Journal. Nov./Dec. 1999: 452-458.

(Continued)

*Primary Examiner* — Navin Natnithithadha
*Assistant Examiner* — Eric Messersmith
(74) *Attorney, Agent, or Firm* — Fasth Law Offices; Rolf Fasth

(57) ABSTRACT

The adjustable massage apparatus has a massage effect of which is based on the suction effect created in connection with the treatment head of the apparatus. The treatment head of the apparatus has a surface which comes into contact with the skin, a frame, and a low-pressure chamber, associated with the surface for creating a low-pressure suction in order to lift the skin. The apparatus has a sensor for measuring characteristics of skin tissue, and elements to automatically adjust the low-pressure suction to the desired value, on the basis of the obtained measurements.

30 Claims, 1 Drawing Sheet

(56) References Cited

U.S. PATENT DOCUMENTS

| | | | |
|---|---|---|---|
| 6,117,094 A * | 9/2000 | Fujii | 601/99 |
| 6,309,364 B1 * | 10/2001 | Cathaud et al. | 601/7 |
| 6,796,950 B1 * | 9/2004 | Muller | 601/112 |
| 2002/0058902 A1 * | 5/2002 | Kollias et al. | 604/20 |
| 2003/0073937 A1 | 4/2003 | Guitay | |
| 2004/0210214 A1 * | 10/2004 | Knowlton | 606/41 |
| 2005/0038448 A1 | 2/2005 | Chung | |
| 2005/0119594 A1 | 6/2005 | Piana et al. | |
| 2005/0251118 A1 * | 11/2005 | Anderson et al. | 606/9 |
| 2006/0100555 A1 * | 5/2006 | Cagle et al. | 601/6 |
| 2007/0027411 A1 * | 2/2007 | Ella et al. | 601/7 |

FOREIGN PATENT DOCUMENTS

| | | | |
|---|---|---|---|
| EP | 627662 | | 2/2006 |
| EP | 1627662 | | 2/2006 |
| GB | 395302 | * | 7/1933 |
| JP | 710825 | | 9/1995 |
| JP | 08252286 | | 10/1996 |
| JP | 2001258965 | | 9/2001 |
| JP | 2002282232 | | 10/2002 |
| WO | 0023031 | | 4/2000 |
| WO | 0023032 | | 4/2000 |
| WO | 0193799 | | 12/2001 |
| WO | 03005921 | | 1/2003 |

OTHER PUBLICATIONS

Lambruschi, Phillip G., "Endermologie Revisited (Letter to the Editor)." Aesthetic Surgery Journal. Nov./Dec. 1999: 136-137.

Shack, Bruce R., "Enermologie: Taking a Closer Look." Aesthetic Surgery Journal. May/Jun. 2001: 259-260.

Ersek, Robert A., "Noninvasive Mechanical Body Contouring: A Preliminary Clinical Outcome Study." Aesthetic Plastic Surgery vol. 21: 61-67 1997.

* cited by examiner

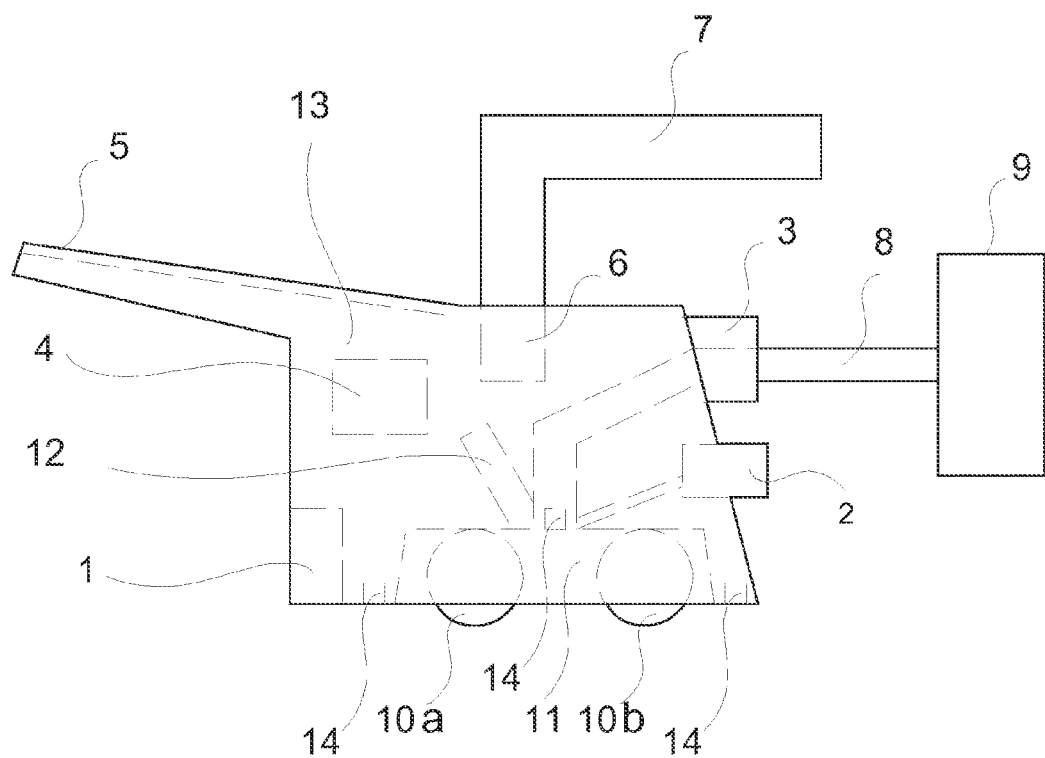

MASSAGE APPARATUS

PRIOR APPLICATIONS

This is a US national phase patent application that claims priority from PCT/FI2006/000343 filed 24 Oct. 2006, that claims priority from Finnish Patent Application Nos. 20051102, filed 31 Oct. 2005, 20060222, filed 7 Mar. 2006 and 20060708, filed 1 Aug. 2006.

FIELD OF THE INVENTION

The purpose of the invention is an adjustable massage apparatus, the massage effect of which is based on the suction effect created in association with at least one roller, located on the frame of the apparatus.

BACKGROUND OF THE INVENTION

Massage affects skin and muscles in many different ways. Massage is a pressing movement applied to soft tissues for treatment purposes, and it is performed in the form of stroking, rubbing, squeezing and different types of tapping. Traditionally, massage aims at improving the metabolism of musculoskeletal and locomotor systems, relaxing the tension of muscles and maintaining working capacity.

Today, massage is increasingly performed using different types of devices, in which case massage is also used for such purposes as plastic and corrective treatment, rheumatic problems, burn injuries, treatment of blood circulation problems, treatment of swelling and cellulite, stimulation of the circulation of lymphatic fluids, for relaxing and firming the tissues and treatment of fibromyalgia. Subcutaneous suction massage of fat and connective tissues stimulates metabolism, blood circulation and restores firmness of tissues and removes cellulite, swelling and muscle tension. The treatment also produces positive results for fibromyalgia pains, scar tissue problems, conditions resulting from sports activities, insomnia and stress.

The method of massage depends on the treatment to be performed. Suction roller treatment is used especially for treating skin problems such as cellulite and swelling. It is performed using a device consisting of a treatment head, which is moved on top of the skin. This treatment head is connected to the suction apparatus with a flexible cord in order to create a vacuum on the skin as the treatment head moves against the patient's body.

The suction roller apparatus comprises rollers, in between which there is a suction chamber which is open at the bottom, into which the skin is sucked, creating a bulge in the skin. The fold of skin formed from the bulge is pressed between the rollers against roller surfaces.

Massage force is most often only determined on the basis of the treatment being given, or by the therapist's touch, or from an idea about what massage force would be suitable to use. Injuries which have to be treated, however, are different, and also different people react in different ways. If there is too little force used in the massage, the treatment will be ineffective, whereas the use of too much force will often lead to tissue damage, bruises and aching.

Moreover, the suction roller apparatuses are difficult to use, with correct use of the apparatuses demanding extensive experience, and acquiring a good "touch" takes years. We refer, for example, to the article "Endermologie: Taking a Closer Look", published in the May-April 2001 issue of Aestethic Surgery Journal, which asserts that the massage force may vary greatly with different users, and that treatment results are mostly dependent on the therapist. Also, the article "Noninvasive Mechanical Body Countouring: A preliminary Clinical Outcome Study" in the Aesthetic Plastic Surgery issue 21:61-67, 1997, asserts that the suction roller treatment is highly user-dependent and may lead to bruises if the massage force is too great, but that the treatment is efficient if the therapist is skillful. With regard to this we also refer to articles published in the 1999 issues of Aesthetic Surgery Journal: "Endermologie Revisited" in the March-April issue, and "Endermologie versus Liposuction with External Ultrasound Assist" in the November-December issue.

Massage apparatuses which are adjustable according to the level of technology are presented in US patent application 2003/0073937. In an apparatus according to this patent, negative pressure and massage force are adjusted at the user's discretion according to the purpose of the massage. In U.S. Pat. No. 5,885,232, the suction force is adjusted in the massage apparatus by maintaining the value in the preset value.

The apparatuses which use the latest technology, do not take into account the personal characteristics of the patient being treated, which is one of the purposes of this invention. Moreover, the purpose is to develop an apparatus which is easier to use than the apparatuses of the latest technology.

DESCRIPTION OF THE INVENTION

The purpose of the invention is an adjustable massage apparatus, the massage effect of which is based on the suction effect created in association with the treatment head. The treatment head of the apparatus comprises a surface which comes in contact with the skin, a frame, and a low-pressure chamber positioned in connection with this surface in order to create a low-pressure suction to lift the skin. The apparatus is mostly characterized in that it has a sensor for measuring one or more characteristics of the skin tissue, and a means to automatically adjust the low-pressure suction to the desired value, based on the results measured by the sensor.

An advantageous embodiment of the invention comprises two rollers, which are in connection with the apparatus frame, between which negative pressure is formed in the low-pressure chamber. The rollers may move against the skin surface, but they may also be static, which means that in one embodiment only one roller moves and the other stays in place, which is advantageous when the front roller, moving in the direction of treatment, stays in place and the back roller moves in order to produce a pinching effect. Also, there can be one or more rollers. In other types of embodiments, the treatment head may just have a cavity at the low-pressure chamber, or sliding surfaces can be used instead of rollers.

Thus, a massage apparatus according to the invention comprises advantageously different sensors, one of which, for example, measures the composition of the skin tissue, such as fluid content, and advantageously also fat and oil contents. Two sensors may also be used for measuring fluid and fat contents. The second sensor, for example, measures the raised skin (bulge) produced by the suction effect, and the third sensor measures, for example, the massage force applied to the skin. The low-pressure suction and massage force are adjusted according to the results of the measurements. The massage apparatus may also comprise a fourth sensor, which measures the skin temperature, and other sensors measuring the characteristics mentioned below. The low-pressure suction and massage force are then adjusted according to the measurement results obtained by these sensors. One sensor measures either one characteristic or several characteristics. Each sensor may be connected to the apparatus either through a wired or wireless connection, such as a radio frequency signal, infrared signal or the like. Thus, the sensors may be an integrated part of the apparatus or separate components.

The adjustment is based on mechanical characteristics and/or electrical characteristics and/or structure and/or composition of the skin. Mechanical characteristics include strength, flexibility, elasticity and resilience etc. Electrical characteristics include, for example, capacitance, impedance, resistance, reactance and inductance.

Moreover, adjustment of this invention can be based on the flow of lymphatic fluid. Measuring techniques for the flow of lymphatic fluid are selected from known technologies.

In addition, the apparatus may comprise a sensor for measuring the skin's blood circulation, the measurements of which determine the adjustment.

Furthermore adjustment may be based on the measurement of transepidermal water loss and skin pH.

Adjustments may also be based on the measurement of the patient's experience of cutaneous pain. In this case, the patient himself/herself, or the therapist, or both together adjust the apparatus's running parameters. Skin characteristics, when mentioned in this text, also include the pain felt and experienced on the skin. The skin refers to all skin layers i.e. epidermis, dermis, hypodermis or subcutis. The apparatus may comprise a sensor which registers a signal given by the patient for increasing/decreasing the suction effect, and which triggers the adjustment. The patient may thus give a signal to the sensor (for example, based on the pain experienced) and the sensor then relays to the apparatus the wish for the increase/decrease in suction.

The apparatus may also comprise other energy sources for warming the skin tissue and furthermore, means for automatically adjusting these energy sources to the desired value, based on the measurements obtained by one or more sensors.

Measuring techniques include the measurement of different sound frequencies, such as ultrasound and infrasound, techniques based on radio frequencies and on different wave lengths of light i.e. optical measurement such as laser and infrared measurement, bioimpedance spectroscopy, magnetic resonance spectroscopy, raman spectroscopy, nuclear magnetic resonance spectroscopy, microsensor mapping, heat camera imaging, spectrofotometric intracutaneus imagining.

A computer program guides the masseur in the application of force by presenting the force level visually in the treatment head and/or in the external display. Low-pressure suction is adjusted automatically using the computer program, and thus it is not necessary for the masseur to adjust the low-pressure suction during the treatment. Advantageously, when the massage force exceeds the permitted value, the program stops the apparatus.

By monitoring the measurements, it is possible for the masseur to achieve an optimal or the best massaging result without skin or tissue damages. The massage performance is nearly independent of the therapist's skills when considering the subcutaneous fluid content, fat content, skin lift, the massage force applied to the skin and the suction effect.

It is also possible to install a speed measurement in the apparatus which will calculate the optimal treatment speed. The suction can be located inside the rollers which is an entirely novel solution.

The suction force generated from inside the rollers, and the suction sector, i.e. the adjustment of the suction area, can be determined accurately in order to create a desired skin lift for the fold of the skin. This enables a one-roller treatment apparatus. A multi-roller solution is also possible, which makes it possible to control the skin lift even more precisely over a wider area, which also produces suction also between the rollers.

In the following section, the invention will be presented with reference to a certain advantageous embodiment with the use of a FIGURE. The invention shall, however, not be limited to the details of the embodiment. Therefore, as mentioned earlier, the connection of each sensor to the apparatus may vary, within the scope of the invention, for different embodiments of the apparatuses.

BRIEF DESCRIPTION OF THE DRAWING

FIG. 1 illustrates one example of a massage apparatus according to the invention.

DETAILED DESCRIPTION

FIG. 1 illustrates one example of a massage apparatus according to the invention. The massage effect of the massage apparatus is based on the suction effect created between two rollers 10a, 10b located on the frame 13 of an apparatus according to FIG. 1.

The treatment head of the apparatus comprises a frame 13 and two rollers 10a, 10b connected to the bottom part of the frame. The bottom part of the frame 13, where the rollers 10a, 10b are also located, has a low-pressure chamber 11 for low-pressure suction which is generated through the vacuum pipe/hose 8 using a low-pressure pump 9. Necessary adjustment valves are also mounted in the low-pressure pump 9.

As the treatment head of the massage apparatus is moved against the patient's skin, most comfortably using a handle 7, the effect of the low-pressure causes a fold of skin to be pulled up between the rollers 10a, 10b, and into the low-pressure chamber 11.

A computer program automatically calculates and adjusts the level of low-pressure suction to the target value, based on the measurements obtained. The parameters of the measurements, which affect the target value of the low-pressure suction, include fluid content of the skin tissue, fat content of the skin tissue, the bulge i.e. the lift of the skin tissue (the size of the fold in the skin) and/or the skin temperature.

In order to obtain the measurements, the apparatus comprises a sensor 1 for measuring the fluid content and fat content of the skin tissue, a sensor 12 for measuring the lift of the skin tissue, and, optionally, a temperature sensor 14 for measuring the skin temperature. Additionally, the apparatus may comprise one or more elements, which operate as energy sources for treating the tissue, such as for heating, which are based on sound, light, radio frequency or electricity, for example, it can be an infrared sensor, radio frequency sensor (RF), ultrasound sensor, laser or other element that emits monochromatic light, infrasound sensor, electric resistance or electric electrode. These elements may be wired or wireless.

The measurements from one or more sensors are used for automatically adjusting the low-pressure suction and other energy sources to the desired value. Automatic adjustment of the low-pressure suction uses, for example, a control unit 4 with a microprocessor, which is either inside or outside of the apparatus. The control unit 4 receives the desired value of the low-pressure suction from the computer program running in the microprocessor, which calculates the desired value of the low-pressure suction, based on one or more measurements. Furthermore, the control unit has a central memory. The control unit, microprocessor and central unit may be integrated into the treatment head or be separate, or they may be both integrated and separate.

The massage apparatus in FIG. 1 has two or more rollers 10a, 10b, in between which negative pressure is created in the low-pressure chamber 11. It is also possible to use one or more perforated rollers, inside of which negative pressure is created (not presented). The rollers may move against each other during the massage in order to produce a pinching effect, or they may be locked at a determined distance from one another to eliminate the pinching effect.

The computer program calculates the target value of one or more on-going treatment forces, such as massage force, based on the measurements obtained and/or on the desired value of the suction pressure. Therefore, the apparatus also comprises a sensor 6 for measuring one or more on-going treatment forces, such as the level of the massage force.

The treatment head has a display 5 which displays the massage force, and the person performing the treatment may monitor the massage force from the display 5, which shows both the target value (i.e. the desired value) of the massage force and the on-going massage force value, and applies the force accordingly. The program stops the apparatus if the massage force exceeds the permitted value. Furthermore, the program may be joined to the database, which contains the patient's treatment information. The display 5 is in the control panel, which may be integrated into the treatment head, or be separate, or both.

Also, the power of the energy source 14 may be controlled based on the tissue measurements. A temperature sensor 14 may be integrated into the treatment head, or it may be used separately.

While the present invention has been described in accordance with preferred compositions and embodiments, it is to be understood that certain substitutions and alterations may be made thereto without departing from the spirit and scope of the following claims.

The invention claimed is:

1. An adjustable massage apparatus for massaging a patient, a massage effect of which is based on a suction effect created in connection with a treatment head, the adjustable massage apparatus comprising:
    a first sensor configured to measure a lift of the skin tissue,
    a control unit in operative engagement with a treatment head and at least the first sensor, the control unit configured to set, based on measurements from the first sensor, the suction effect provided by the treatment head to the desired value during on-going treatment,
    the treatment head comprising:
        a surface adapted to come into contact with a skin surface of a skin,
        a frame, the treatment head having a low-pressure chamber defined in the frame for generating the suction effect and the lift of the skin tissue; and
        rollers or sliding surfaces for moving the massage apparatus relative to the skin surface while lifting the skin tissue into the low-pressure chamber to provide massage to the skin, the low-pressure chamber being disposed between the rollers or sliding surfaces.

2. A massage apparatus according to claim 1, a sensor for measuring a blood flow of the skin.

3. A massage apparatus according to claim 1 further comprising a second sensor configured to measure mechanical characteristics of the skin.

4. A massage apparatus according to claim 1 further comprising a second sensor configured to measure electrical characteristics of the skin.

5. A massage apparatus according to claim 1 further comprising a second sensor configured to measure a lymphatic fluid flow of the skin.

6. A massage apparatus according to claim 1 further comprising a second sensor configured to measure a blood circulation of the skin.

7. A massage apparatus according to claim 1 further comprising a second sensor configured to measure a water loss of the skin.

8. A massage apparatus according to claim 1 further comprising a second sensor configured to measure pH.

9. A massage apparatus according to claim 1 further comprising a second sensor configured to register a signal given by a patient for increasing/decreasing a treatment effect.

10. A massage apparatus according to claim 1 further comprising a second sensor configured to measure skin temperature.

11. A massage apparatus according to claim 1 wherein the apparatus comprises either a wired or a wireless energy source for treating the skin tissue.

12. A massage apparatus according to claim 1 wherein the apparatus comprises elements for treating the skin tissue.

13. A massage apparatus according to claim 1 wherein the apparatus comprises one or more moving or static rollers connected to the frame and the low-pressure chamber is located between the rollers.

14. A massage apparatus according to claim 1 wherein a surface in the low-pressure chamber comprises a cavity defined therein.

15. A massage apparatus according to claim 1 wherein the apparatus comprises sliding surfaces.

16. A massage apparatus according to claim 1 wherein the apparatus comprises perforated rollers inside of which a negative pressure is created in the low-pressure chamber.

17. A massage apparatus according to claim 13 wherein the rollers are movable towards one another during a massage to produce a pinching effect.

18. A massage apparatus according to claim 17 wherein the rollers are lockable at a certain distance from one another to eliminate the pinching effect.

19. A massage apparatus according to claim 1 wherein the control unit is connected to a microprocessor.

20. A massage apparatus according to claim 19, wherein the control unit is adapted to adjust on-going treatment forces.

21. A massage apparatus according to claim 20 wherein the apparatus comprises a sensor for measuring one or more on-going treatment forces.

22. A massage apparatus according to claim 1 wherein the treatment head comprises a display configured to display a level of one or more on-going treatment forces.

23. A massage apparatus according to claim 22, wherein the display is further configured to display both a targeted level of treatment force and an on-going level of a treatment force.

24. A massage apparatus according to claim 1 wherein the apparatus is stoppable by the control unit when a microprocessor detects that a treatment force exceeds a permitted value.

25. A massage apparatus according to claim 1 wherein a connection of the sensor is either wired or wireless.

26. A massage apparatus according to claim 19 wherein the microprocessor is connected to a database.

27. A massage apparatus according to claim 1 wherein the sensor is based on bio impedance spectroscopy.

28. An adjustable massage apparatus for massaging a patient, a massage effect of which is based on a suction effect created in connection with a treatment head, the adjustable massage apparatus comprising:
  a first skin-characteristics sensor configured to measure elasticity of the skin,
  a control unit in operative engagement with a treatment head and the first skin-characteristics sensor the control unit configured to set, based on measurements from the first skin-characteristics sensor, the suction effect provided by the treatment head to a desired value during on-going treatment,
  the treatment head comprising:
  a surface adapted to come into contact with a skin surface of a skin,
  a frame, the treatment head having a low-pressure chamber defined in the frame for generating the suction effect and a lift of a skin tissue; and
  rollers or sliding surfaces for moving the massage apparatus relative to the skin surface while lifting the skin tissue into the low-pressure chamber to provide massage to the skin, the low-pressure chamber being disposed between the rollers or sliding surfaces.

29. An adjustable massage apparatus for massaging a patient, a massage effect of which is based on a suction effect created in connection with a treatment head, the adjustable massage apparatus comprising:
  a first skin-characteristics sensor configured to measure a temperature of the skin,
  a control unit in operative engagement with a treatment head and the first skin-characteristics sensor the control unit configured to set, based on measurements from the first skin-characteristics sensor, the suction effect provided by the treatment head to a desired value during on-going treatment,
  the treatment head comprising:
  a surface adapted to come into contact with a skin surface of a skin,
  a frame, the treatment head having a low-pressure chamber defined in the frame for generating the suction effect and a lift of a skin tissue; and
  rollers or sliding surfaces for moving the massage apparatus relative to the skin surface while lifting the skin tissue into the low-pressure chamber to provide massage to the skin, the low-pressure chamber being disposed between the rollers or sliding surfaces.

30. An adjustable massage apparatus for massaging a patient, a massage effect of which is based on a suction effect created in connection with a treatment head, the adjustable massage apparatus comprising:
  a first skin-characteristics sensor configured to measure a fluid content of the skin,
  a control unit in operative engagement with a treatment head and the first skin-characteristics sensor the control unit configured to set, based on measurements from the first skin-characteristics sensor, the suction effect provided by the treatment head to a desired value during on-going treatment,
  the treatment head comprising:
  a surface adapted to come into contact with a skin surface of a skin,
  a frame, the treatment head having a low-pressure chamber defined in the frame for generating the suction effect and a lift of a skin tissue; and
  rollers or sliding surfaces for moving the massage apparatus relative to the skin surface while lifting the skin tissue into the low-pressure chamber to provide massage to the skin, the low-pressure chamber being disposed between the rollers or sliding surfaces.

* * * * *